United States Patent
Alani et al.

(10) Patent No.: US 7,267,951 B2
(45) Date of Patent: Sep. 11, 2007

(54) METHOD FOR EVALUATING A TISSUE OR BIOPSY SAMPLE TO DETERMINE IF THE SAMPLE IS EARLY-STAGE MELANOMA

(75) Inventors: Rhoda M. Alani, Baltimore, MD (US); Alison Z. Young, Baltimore, MD (US); Klaus J. Busam, Chatham, NJ (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 373 days.

(21) Appl. No.: 10/453,351

(22) Filed: Jun. 3, 2003

(65) Prior Publication Data

US 2004/0014114 A1  Jan. 22, 2004

Related U.S. Application Data

(60) Provisional application No. 60/386,298, filed on Jun. 5, 2002.

(51) Int. Cl.
*C12Q 1/68* (2006.01)
(52) U.S. Cl. .......................................................... 435/6
(58) Field of Classification Search ..................... None
See application file for complete search history.

(56) References Cited

FOREIGN PATENT DOCUMENTS

WO  WO97/05283 A1  2/1997
WO  WO 01/68784 A1  9/2001

OTHER PUBLICATIONS

Han et al., 2004, Cancer Letters 216:63-71.*
Polsky et al., 2001, Cancer Research 61:6008-6011.*
Kim et al., 2002, Cancer Control 9:9-15.*
Goidin et al., 2001, Analytical Biochemistry 295:17-21.*
Alani et al., Id1 regulation of cellular senescence through transcriptional repression of p16/Ink4a, PNAS, Jul. 3, 2001, pp. 7812-7816, vol. 98, No. 14.
Jen et al., Expression Patterns of ID1, Id2, and Id3 Are Highly Related but Distinct from That of Id4 During Mouse Embryogenesis, Developmental Dynamics, 1996, pp. 235-252, vol.
Jen et al., Each Member of the Id Gene Family Exhibits a Unique Expression Pattern in Mouse Gastrulation and Neurogenesis, Developmental Dynamics, 1997, pp. 92-106, vol. 208.
Lyden et al., ID1 and Id3 are required for neurogenesis, angiogenesis and vascularization of tumour xenografts, Nature, Oct. 14, 1999,—www.nature.com pp. 670-677, vol. 401.
Lyden et al., Impaired recruitment of bone-marrow-derived endothelial and hematopoietic precursor cells blocks tumor angiogenesis and growth, Nature Medicine, Nov. 1, 2001, Page(s).
Manova et al., Apoptosis in Mouse Embryos: Elevated Levels in Pregastrulae and in the Distal Anterior Region of Gastrulae of Normal and Mutant Mice, Developmental Dynamics,.
Mathew et al., Chromosomal Assignment of Human ID1 and ID2 Genes, Genomics, 1995, pp. 385-387, vol. 30.
Pesce et al., The Loop Region of the Helix-Loop-Helix Protein Id1 is Critical for Its Dominant Negative Activity, Molecular and Cellular Biology, 1993, pp. 7874-7880, vol. 13, No. 12.
Polsky et al., The Transcriptional Repressor of p16/Ink4a, Id1, Is Up-Regulated in Early Melanomas, Cancer Research, Aug. 15, 2001, pp. 6008-6011, vol. 61.
Stebbins et al., Crystal Structure of an Hsp90-Geldanamycin Complex: Targeting of a Protein Chaperone by an Antitumor Agent, Molecular Biology, Apr. 18, 1997, pp. 239-250, vol. 89.
Tornay et al., Transcription of the Dominant-Negative Helix-Loop-Helix Protein Id1 is Regulated by a Protein Complex Containing the Immediate-Early Response Gene Egr-1, Molecular and Cellular Biology, May 1, 1996, pp. 2418-2430, vol. 16, No. 5.
Yan et al., High Incidence of T-Cell Tumors in E2A-Null Mice and E2A/Id1 Double-Knockout Mice, Molecular and Cellular Biology, 1997, pp. 7317-7327, vol. 17, No. 12.

* cited by examiner

*Primary Examiner*—Shanon Foley
*Assistant Examiner*—Catherine Joyce
(74) *Attorney, Agent, or Firm*—Marina Larson & Associates, LLC

(57) ABSTRACT

A tissue or biopsy sample is evaluated to determine if the sample is early-stage melanoma by determining the level of inhibitor of DNA-binding protein 1 (Id1) expression in cells of the sample; and comparing the determined amount of Id1 to a reference level. The presence of levels of Id1 in cells of the sample in excess of the reference level indicates that the sample is early-stage melanoma.

10 Claims, No Drawings

SEQUENCE LISTING

<160> NUMBER OF SEQ ID NOS: 2

<210> SEQ ID NO 1
<211> LENGTH: 958
<212> TYPE: DNA
<213> ORGANISM: artificial
<220> FEATURE:
<223> OTHER INFORMATION: probe for Id1

<400> SEQUENCE: 1
ttcgggcttc cacctcattt ttttcgcttt gcccattctg tttcagccag tcgccaagaa    60

-continued

```
tcatgaaagt cgccagtggc agcaccgcca ccgccgccgc gggccccagc tgcgcgctga    120
aggccggcaa gacagcgagc ggtgcgggcg aggtggtgcg ctgtctgtct gagcagagcg    180
tggccatctc gcgctgcgcc gggggcgccg gggcgcgcct gcctgccctg ctggacgagc    240
agcaggtaaa cgtgctgctc tacgacatga acggctgtta ctcacgcctc aaggagctgg    300
tgcccaccct gccccagaac cgcaaggtga gcaaggtgga gattctccag cacgtcatcg    360
actacatcag ggaccttcag ttggagctga actcggaatc cgaagttgga accccgggg     420 gccgagggct gccggtccgg gctccgctca gcaccctcaa cggcgagatc agcgccctga    480
cggccgaggt gagatccaga tccgaccact agatcatcct tataccgacg gggaaacgga    540
ggccagagag ggcgtgggcg cttgcaccac ttccgtccca tccttgcggg tacctggcta    600
tgcgggggtg cctaaggagc ctggaaaaag cgctccccg tcgtgcttcc tggggaaggg     660
ggcgttcgct gcgctcggag cggcgtccct tccaacccgc cggtctcatt tcttctcgtt    720
ttcacaggcg gcatgcgttc ctgcggacga tcgcatcttg tgtcgctgaa gcgcctcccc    780
cagggaccgg cggaccccag ccatccaggg ggcaagagga attacgtgct ctgtgggtct    840
cccccaacgc gcctcgccgg atctgaggga gaacaagacc gatcggcggc cactgcgccc    900
ttaactgcat ccagcctggg gctgaggctg aggcactggc gaggagaggg cgctcctc     958
```

<210> SEQ ID NO 2
<211> LENGTH: 147
<212> TYPE: DNA
<213> ORGANISM: artificial
<220> FEATURE:
<223> OTHER INFORMATION: probe for Id1

<400> SEQUENCE: 2

```
caccctcaac ggcgagatca gcgccctgac ggccgaggcg gcatgcgttc ctgcggacga    60
tcgcatcttg tgtcgctgaa gcgcctcccc cagggaccgg cggaccccag ccatccaggg   120
ggcaagagga attacgtgct ctgtggg                                       147
```

METHOD FOR EVALUATING A TISSUE OR BIOPSY SAMPLE TO DETERMINE IF THE SAMPLE IS EARLY-STAGE MELANOMA

This application claims the benefit of U.S. Provisional Application No. 60/386,298, filed Jun. 5, 2002, which is incorporated herein by reference.

This work was supported by NIH Grant No. AR01975. The United States government may have certain rights in the invention.

BACKGROUND OF THE INVENTION

This application relates to a method for evaluating a tissue of biopsy sample to determine if the sample is early stage melanoma. The method relies on the observation that Id1 protein, one of a class of Id proteins which inhibit DNA binding by transcriptional regulatory proteins, is expressed in early stage melanomas, but not in benign specimens nor in invasive or metastatic melanomas. In tumors with in situ and invasive portions, only the in situ part of the tumor expresses Id1.

It has previously been shown in Published PCT Application WO97/05283, which is incorporated herein by reference, that Id proteins, or the nucleic acids encoding such proteins, can serve as diagnostic markers for identifying tumors which may be susceptible to treatment by chemotherapy and radiation. This patent shows data suggesting the ability to use Id1 to distinguish between rhabdomyosarcoma (RMS) and normal muscle cells, but offers no insight concerning melanoma.

SUMMARY OF THE INVENTION

The present invention provides a method for evaluating a tissue of biopsy sample to determine if the sample is early-stage melanoma. The method comprises the steps of:

(a) determining the level of Id1 expression in cells of the sample; and (b) comparing the determined amount of Id1 to a reference level, wherein the presence of levels of Id1 in cells of the sample in excess of the reference level indicates that the sample is early-stage melanoma.

DETAILED DESCRIPTION OF THE INVENTION

The present invention provides a method for evaluating a tissue of biopsy sample to determine if the sample is early-stage melanoma, comprising the steps of:

(a) determining the level of Id1 expression in cells of the sample; and (b) comparing the determined amount of Id1 to a reference level, wherein the presence of levels of Id1 in cells of the sample in excess of the reference level indicates that the sample is early-stage melanoma.

Suitable samples to which the method of the invention may be applied include cutaneous tissue and biopsy specimens taken from mammalian subjects, including human subjects, where there is a concern that the sample may be malignant melanoma. Particular samples are those taken from skin lesions, moles, and other cutaneous irregularities.

The step of determining the amount of Id1 present in cells of the sample may be accomplished by any of a number of methods which are known generally in the art. For example, the amount if Id1 may be determined by immunological techniques, where an antibody specific for Id1 is utilized as a detection reagent. The Id1-specific antibody is labeled, directly or indirectly (for example as a result of formation of a complex with a non-Id1-specific labeled reagent) with a colored, fluorescent, chromogenic, fluorogenic (including chemiluminescent), radioactive or other suitable label. The format of the assay may be a direct binding assay or a sandwich assay, such as Western Blot or ELISA. The antibodies used in such assays may be polyclonal or monoclonal antibodies, and can be generated using known methods.

The amount of Id1 in the sample may also be determined by measurement of mRNA encoding Id1. Isolation of mRNA fractions from cells is performed using known method. The mRNA may then be analyzed directly (for example by sequence specific hybridization assays, optionally with signal amplification) or may be reverse transcribed and amplified, for example using PCR, prior to quantitation of the amount of Id1 mRNA. The amount of Id1 in the sample may also be determined by in situ hybrodization using a cRNA probe. As will be appreciated, the specific sequence of such a probe is not critical, provided it is complementary to a diagnostic portion of Id1.

One suitable sequence for this purpose is that of Seq. ID No: 1. This sequence represents 958 nucleotides of the human Id1 cDNA and includes 62 nucleotides of the 5' untranslated region. Another probe that can be used is that set forth in Seq ID No: 2. Other probes which can be used for oligonucleotide-based in-situ probes that are useful for detection of Id1 expression can be used in the method of the invention. (See, for example, Langlands et. al., Cancer Research (2000) 60:5929-5933, which is incorporated herein by reference). The probe sequence used in detection of mRNA or amplified DNA is suitably labeled with a colored, fluorescent, chromogenic, fluorogenic (including chemiluminescent), radioactive or other label.

Determination of levels of Id1 expression can also be accomplished through immunoassay procedures using an Id1 specific antibody. For example, many people have published that the Santa Cruz sc-488 antibody is specific for Id1 in immunohistochemical analyses and has potential utility in the present invention.

The second step of the method of the invention is comparing the determined amount of Id1 in the sample to a reference level. As used in this application, this comparison, and the reference level may be a simple binary comparison, i.e., detected versus not detected, with not detected serving as the reference level. The comparison may also be a comparison between a measured level and a numerical threshold which is determined to be representative of a negative result for the assay being employed. The comparison may also be made to a reference level determined by concurrent evaluation of a control sample, known to be negative for Id1, or an apparently normal epidermal tissue sample obtained from the same source (subject) as a sample suspected of being melanoma. Combinations of each of these comparisons may also be employed. In each of these embodiments, the presence of levels of Id1 in cells of the sample in excess of the reference level by a statistically relevant amount indicates that the sample is early stage melanoma.

The method of the present invention may be conveniently practiced using a diagnostic kit. Such a kit comprises reagents specific for the detection of Id1 in the tissue sample (either as expressed protein or mRNA). In addition, the kit includes appropriate printed instructions for comparison of the determined amount of Id1 with a reference standard. The reference standard is provided in the kit in the form of at least one of: (a) a specific numerical threshold determined by the characteristics of the kit, including in some cases a threshold which is a reagent lot-specific value; (b) a negative control sample for concurrent evaluation with the tissue or biopsy sample, and optionally a positive control; or (c) statistical information to allow comparison of a subject-derived control and a subject-derived sample.

Where the kit contains a specific numerical threshold printed as part of the instructions, the numerical threshold is determined for the specific reagents in the kit by conducting a series of tests using the reagents in the kit on known negative samples, and known positive samples, preferably with different levels of Id1. Similar comparisons are appropriately used in determining the statistical information for comparison of subject-derived sample and a negative control. In one embodiment of the invention, a positive control is also used. For example, metastic melanoma, in which there is clear perivascular expression of Id1 resulting in distinctive perivascular staining, can be used as a positive control.

We have also observed that Id1 expression appears to be critically involved in the progression of in situ melanoma to an invasive and metastatic stage. In particular, Id1 expression correlates with decreased expression of the p16/Ink4a gene in early melanomas that are confined to the radial growth phase. This supports the conclusion that Id1 transcriptional repression of p16/Ink4a represents one of the earliest mechanisms of dysregulation of p16 expression in melanoma initiation. Thus, limiting or eliminating Id1 expression may serve to retard progression of cells to melanoma and progression of melanoma, and offers a possibility for post-surgery prophylactic therapy. For example, antisense therapy directed against Id1 expression may be used in a topical agent. Antibody therapy may also be employed. Since the skin is an easily accessible organ, either topical therapy or local injection of therapies is readily achieved.

EXAMPLE 1

Archival samples of five common melanocytic nevi, five atypical (dysplastic) nevi, six primary cutaneous melanomas of different thickness and level of invasion and five metastatic lesions were evaluated by immunohistochemical analysis for p16 levels, and by in situ hybridization for Id1 levels.

For immunohistochemical analysis, 6-7 micron sections were blocked with 10% normal horse serum (Vector) in PBS-TZ and incubated with monoclonal anti-p16 (Santa Cruz Biotechnology) antibody diluted 1:250 or with polyclonal anti-p19 (AEC40, gift from N. Sharpless and R. DePinho, Dana Farber Cancer Institute) diluted 1:200 in PBS-TX with 1% normal horse serum. Section were then incubated with biotinylated horse antimouse secondary antibody (Vector) diluted 1:200 in PBS with ⅕% normal horse serum. A Vectastain Elite ABC kit (Vector) was used for horseradish peroxidase staining of the sections.

For in situ hybridization, 6-7 micron sections were processed with [α-$^{33}$P}UP-labeled cRNA probes of Seq. ID No: 2. The general procedure used was a previously described in Lyden et al., *Nature (Lond)* 401: 670-677 (1999), which is incorporated herein by reference.

As had been previously reported (Reed et al., *Cancer Res.* 55: 2713-2718 (1995); Funk et al., *J. Cutan. Pathol.* 25: 291-296 (1998)), decreasing p16 expression was observed as a function of increasing malignant potential, with 70-90% of p16 positivity in compound and dysplastic nevi, 30-50% positivity in in situ and malignant melanomas, and less than 10% positivity in metastatic lesions. In contrast, in situ evaluation of Id1 expression in these lesions demonstrated no Id1 expression in either compound or dysplastic nevi, but marked Id1 expression in both the intraepidermal (in situ) melanoma component and neighboring keratinocytes. The invasive components of these melanomas were not observed to express significantly elevated Id1 expression. Metastatic melanomas exhibited significantly elevated Id1 expression only around the vasculature within the lesions as has been previously observed in other malignancies. Lyden et al., *Nature (Lond)* 401: 670-677 (1999). These demonstrate the ability of Id1 to serve as a marker of early stage melanoma. The results further suggest that Id1 may play an important role in early melanomagenesis, but is not likely to be necessary for invasion or metastasis of this tumor.

EXAMPLE 2

Samples of melanoma cell lines from tumors of varying degrees of invasiveness were kindly provided by Meenhard Herlyn of the Wistar Institute, and were evaluated for expression of Id1 and PCNA (a marker of cellular proliferation) by Western analysis. Three samples were cell lines derived from radial-growth-phase melanoma, a non-invasive early stage of melanoma; 3 samples from more advanced vertical growth phase melanomas and three from metastatic melanoma. Normal human melanocytes and mouse embryo fibroblasts for wildtype (+/+) and Id1 knockout mice were used as controls.

All radial-growth-phase melanoma cell lines evaluated possess elevated Id1 expression while normal human melanocytes (Mel) and invasive melanomas did not express detectable amounts of Id1 protein.

The invention claimed is:

1. A method for evaluating a tissue of biopsy sample to determine if the sample is melanoma in situ, comprising the steps of:
   (a) determining the level of inhibitor of DNA-binding protein (Id1) expression in cells of the sample; and
   (b) comparing the determined amount of Id1 to a reference level representative of normal, non-cancerous epidermal cells, wherein the presence of levels of Id1 in cells of the sample in excess of the reference level indicates that the sample is melanoma in situ.

2. The method of claim 1, wherein the amount of Id1 is determined using antibody specific for Id1 as a detection reagent.

3. The method of claim 2, wherein the Id1-specific antibody is labeled, directly or indirectly.

4. The method of claim 3, wherein the label is a colored, fluorescent, chromogenic, fluorogenic or radioactive label.

5. The method of claim 2, wherein the Id1-specific antibody is used in a direct binding assay.

6. The method of claim 2, wherein the Id1-specific antibody is used in a sandwich assay.

7. The method of claim 1, wherein the amount of Id1 is determined by measuring the amount of Id1 mRNA using a sequence specific oligonucleotide probe.

8. The method of claim 7, wherein the amount of Id1 mRNA is determined by in situ hybridization with a cRNA probe.

9. The method of claim 8, wherein the cRNA probe is labeled with a colored, fluorescent, chromogenic, fluorogenic or radioactive label.

10. The method according to claim 7, wherein the Id1 mRNA is converted to DNA by reverse transcription and amplified prior to hybridization with the sequence-specific oligonucleotide probe.

* * * * *

UNITED STATES PATENT AND TRADEMARK OFFICE
CERTIFICATE OF CORRECTION

| | |
|---|---|
| PATENT NO. | : 7,267,951 B2 |
| APPLICATION NO. | : 10/453351 |
| DATED | : September 11, 2007 |
| INVENTOR(S) | : Alani et al. |

Page 1 of 1

It is certified that error appears in the above-identified patent and that said Letters Patent is hereby corrected as shown below:

Column 1, Lines 8-10: insert --This work was supported by NIH Grant No.: GM56425. The United States government has certain rights in the invention--.

Signed and Sealed this

Eighteenth Day of March, 2008

JON W. DUDAS
*Director of the United States Patent and Trademark Office*